(12) United States Patent
Kirby et al.

(10) Patent No.: US 8,541,718 B2
(45) Date of Patent: Sep. 24, 2013

(54) HYPODERMIC NEEDLE DESTRUCTION

(75) Inventors: Clifford Ian Kirby, Merseyside (GB); Norman Trevor Douce, Merseyside (GB)

(73) Assignee: Needlesmart Holdings Limited, West Midlands (GB)

( * ) Notice: Subject to any disclaimer, the term of this patent is extended or adjusted under 35 U.S.C. 154(b) by 123 days.

(21) Appl. No.: 13/146,718

(22) PCT Filed: Jan. 29, 2010

(86) PCT No.: PCT/GB2010/050143
§ 371 (c)(1),
(2), (4) Date: Jul. 28, 2011

(87) PCT Pub. No.: WO2010/086665
PCT Pub. Date: Aug. 5, 2010

(65) Prior Publication Data
US 2011/0278281 A1    Nov. 17, 2011

(51) Int. Cl.
*H05B 1/02*    (2006.01)
(52) U.S. Cl.
USPC ............................ 219/492; 219/494; 219/490
(58) Field of Classification Search
CPC ....................................................... H05B 1/02
USPC .............. 219/490–494, 497, 121.37, 121.48, 219/68
See application file for complete search history.

(56) References Cited

U.S. PATENT DOCUMENTS

| | | | | |
|---|---|---|---|---|
| 4,860,958 A | * | 8/1989 | Yerman | 241/23 |
| 4,877,934 A | | 10/1989 | Spinello | |
| 5,075,529 A | | 12/1991 | Kudo | |
| 5,268,549 A | * | 12/1993 | Butler | 219/68 |
| 5,288,964 A | | 2/1994 | Walker et al. | |
| 5,300,752 A | | 4/1994 | Elmerick et al. | |
| 5,329,087 A | * | 7/1994 | Kohl et al. | 219/68 |
| 5,468,928 A | * | 11/1995 | Yelvington | 219/68 |
| 5,741,230 A | * | 4/1998 | Miller | 604/110 |
| 5,877,469 A | * | 3/1999 | Truesdale et al. | 219/68 |
| 6,169,260 B1 | * | 1/2001 | Akutsu et al. | 219/68 |
| 6,376,792 B1 | * | 4/2002 | Cebollero et al. | 219/68 |
| 6,580,047 B1 | * | 6/2003 | Smith | 219/68 |
| 2003/0010754 A1 | * | 1/2003 | Adkins | 219/69.15 |

FOREIGN PATENT DOCUMENTS

| | | |
|---|---|---|
| CA | 2209210 A1 | 12/1998 |
| JP | 6254144 A | 9/1994 |
| WO | 9428852 A1 | 12/1994 |
| WO | 9839129 A1 | 9/1998 |
| WO | 0158637 A1 | 8/2001 |

OTHER PUBLICATIONS

EP Intellectual Property Office, Search Report under Section 17(5) for Application No. GB0901530.6 dated May 12, 2009, 3 pages.

* cited by examiner

*Primary Examiner* — Mark Paschall
(74) *Attorney, Agent, or Firm* — Stephen F. Swinton, Jr.; Hoffman Warnick LLC

(57) ABSTRACT

Disclosed is an apparatus for processing a hypodermic needle (2), comprising: means for softening the needle; and means (120) for providing a compressive force to the needle.

15 Claims, 18 Drawing Sheets

US 8,541,718 B2

1

HYPODERMIC NEEDLE DESTRUCTION

The present invention is related to an apparatus and method related to the safe destruction of used hypodermic needles as used in medicine and dentistry for injecting patients.

Generally, once a hypodermic needle has been used to administer a drug to a patient, or to remove a blood sample from a patient, the entire syringe assembly including the hypodermic needle is disposed of so it may not be used again and to ensure that infections are not transmitted from one patient to another. In present practice, the entire assembly is disposed of in what is termed a 'sharps' bin, where it is treated as hazardous medical waste and handled and disposed of accordingly. Health and Safety procedures do not generally allow the needle to be removed from the syringe after use, as this is a likely way for an injury to occur.

In some specialised applications, especially in dentistry, a metal-bodied syringe is used. This can be re-used after suitable treatment, but the problem of needle disposal still pertains.

However, there are problems associated with the safe disposal of hypodermic needles. Once a hypodermic needle has been used, there is a chance that the practitioner can inadvertently pierce their skin, or that of a colleague, with the needle whilst transporting it to the sharps bin. Such an injury is known as a needlestick injury. This can cause the practitioner to become inoculated with one or more possibly dangerous pathogens from the patient in question.

Some pathogens to which a practitioner could be exposed in this way can be very dangerous and could be career-limiting or even potentially life threatening. Examples of these include hepatitis and HIV, although there are a great many more. If the practitioner becomes infected with one or more of these conditions, then the treatment can involve a lengthy course of medicines, including antiretroviral drugs, the side effects of which can be dangerous and unpleasant in themselves. In recent times, several health care professionals have died after becoming infected directly from needlestick injuries. Many more have had to change career as a direct result of needlestick injuries.

Other locations where individuals can come into contact with potentially dangerous used syringes include areas frequented by drug users, needle exchanges, and households including persons who self-medicate for certain conditions e.g. diabetes.

A further problem with disposing of used hypodermic needles is the special handling requirements associated with used needles and the cost involved in disposing of them safely. As mentioned, once a used hypodermic needle is disposed of in a sharps bin, that sharps bin requires special handling to ensure that the potentially dangerous contents cannot injure anybody. Some injuries have resulted from individuals being exposed to dangerous needles from damaged sharps bins.

In a typical hospital environment, the cost and complexity of the disposal of large numbers of such sharps bins can be very high indeed. Across the whole of the UK's National Health Service, many millions of sharps bins are supplied, used and then incinerated each year. This involves considerable expense and contributes to environmental pollution.

Prior art proposals to dispose of used hypodermic needles generally fall short of the required solution and do not fully address the problems associated with safely disposing of used needles. Often, prior art solutions attempt to destroy the needle by the passage of a high electrical current that effectively incinerates the needle. This requires complex equipment, which still leaves the problem of disposing of the residue left by the incineration process. Still other prior art solutions merely bend the tip of the needle, leaving it in a state where it could still injure someone and which would probably still require treating as a 'sharp' under Health and Safety rules.

There therefore exists a need to handle and dispose of used hypodermic needles in a safer and more cost effective way. Embodiments of the present invention aim to address this and other problems with the prior art, whether such problems are mentioned herein or not.

According to the present invention there is provided an apparatus and method as set forth in the appended claims. Other features of the invention will be apparent from the dependent claims, and the description which follows.

For a better understanding of the invention, and to show how embodiments of the same may be carried into effect, reference will now be made, by way of example, to the accompanying diagrammatic drawings in which.

Figure 4:
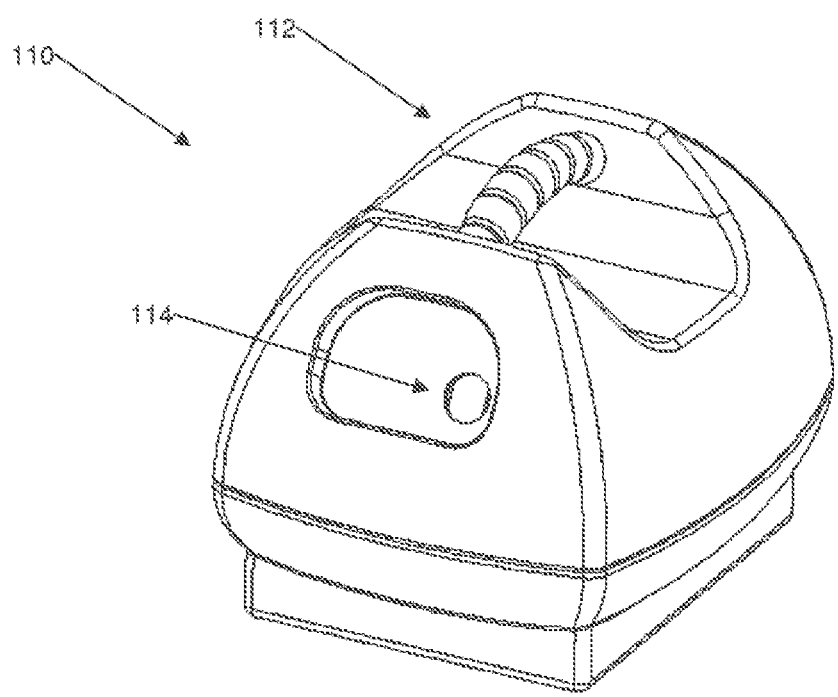
Figure 5:
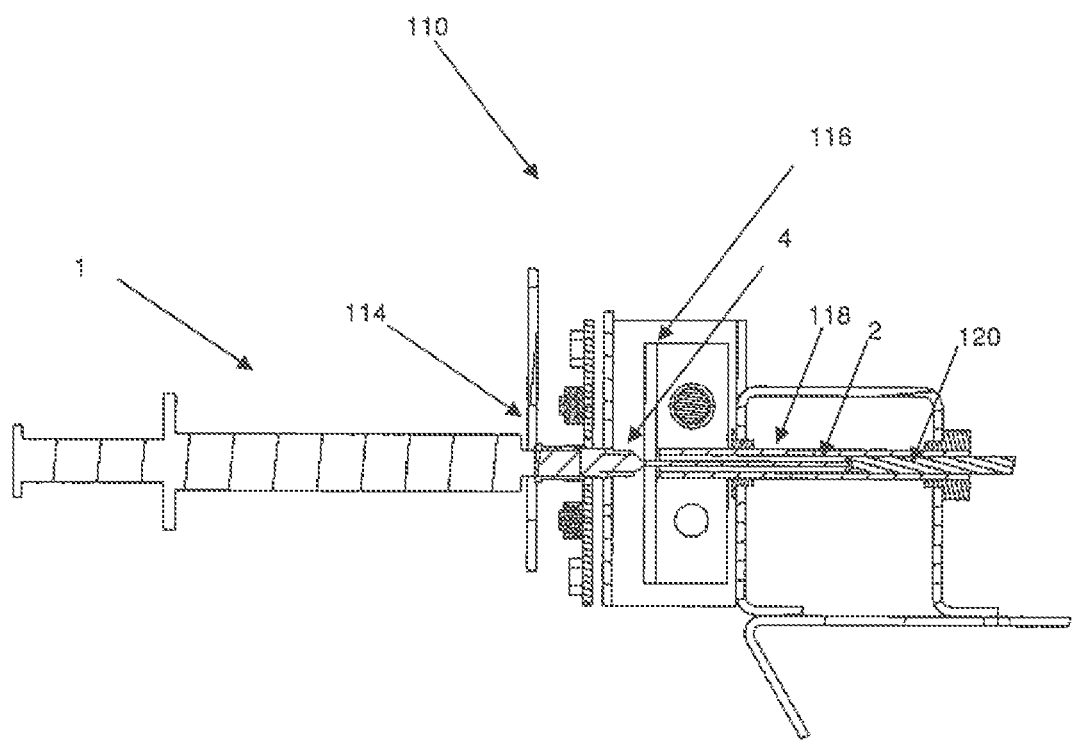
Figure 6:
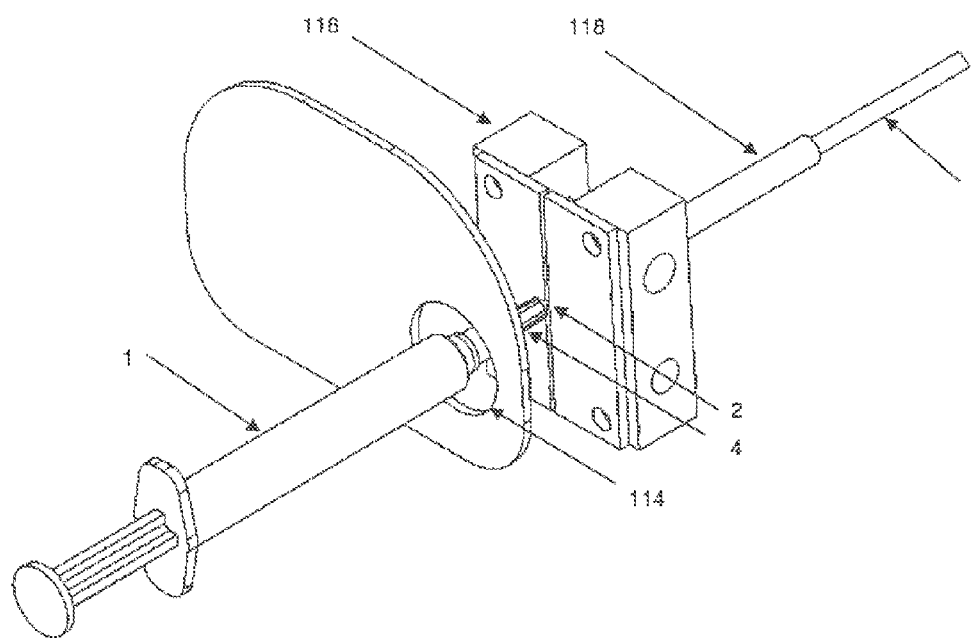
Figure 7:
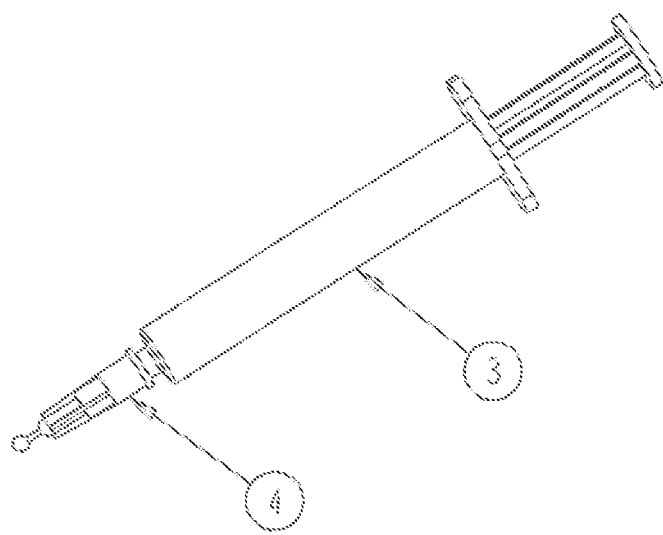
Figure 8:
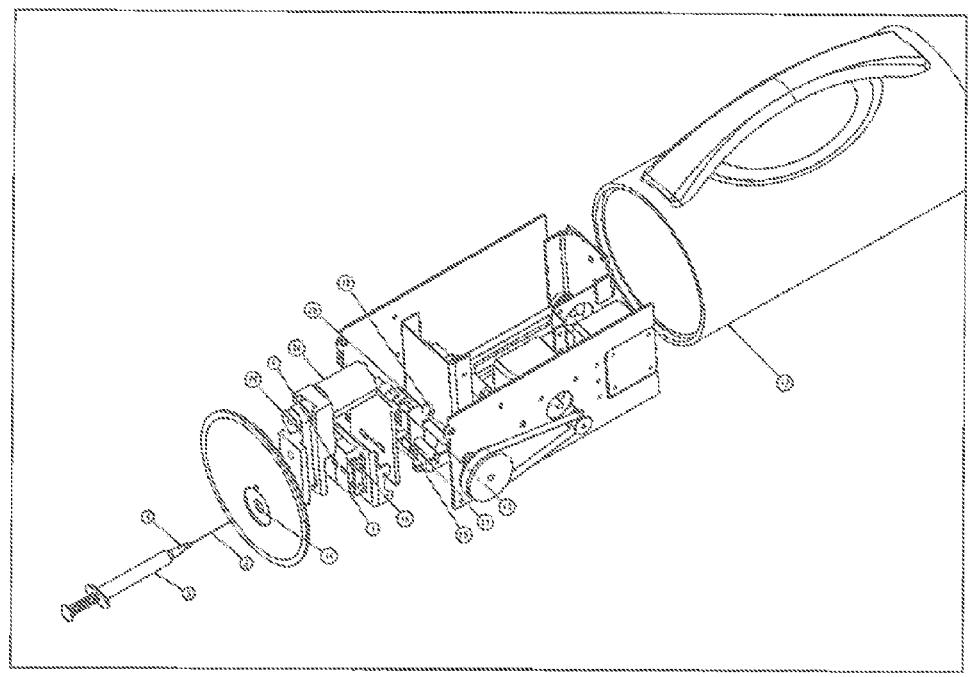
Figure 9:
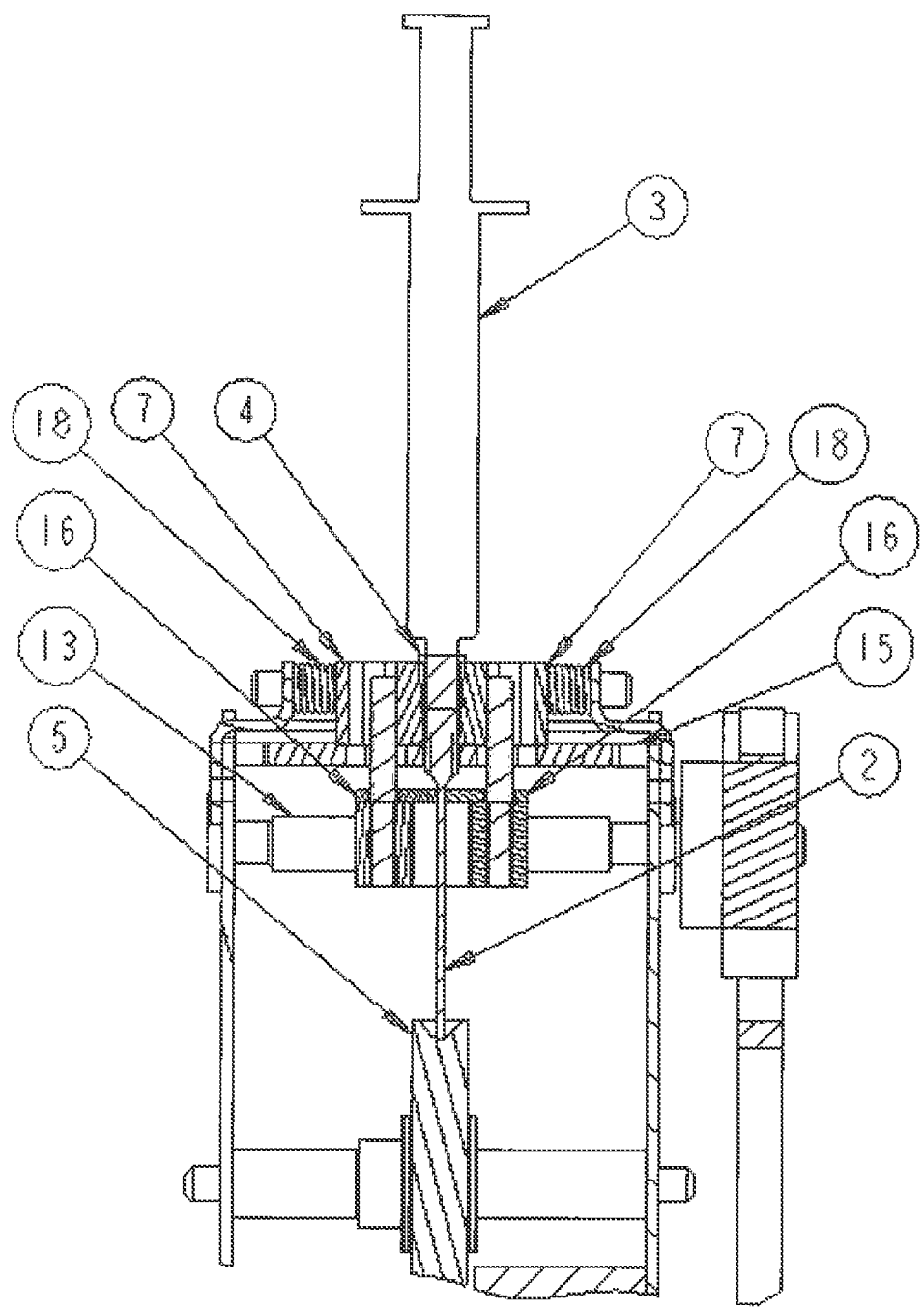
Figure 10:
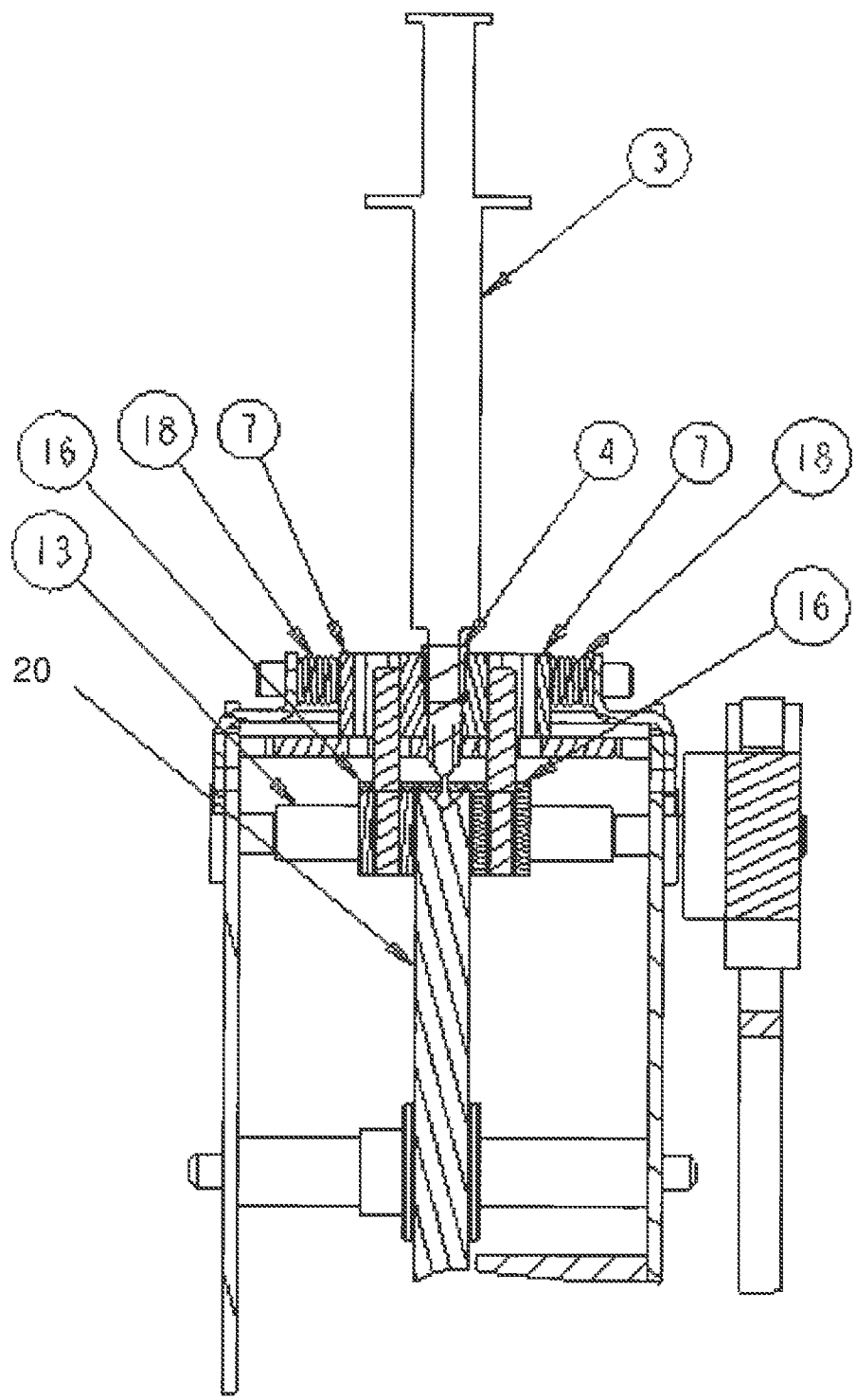
Figure 11:
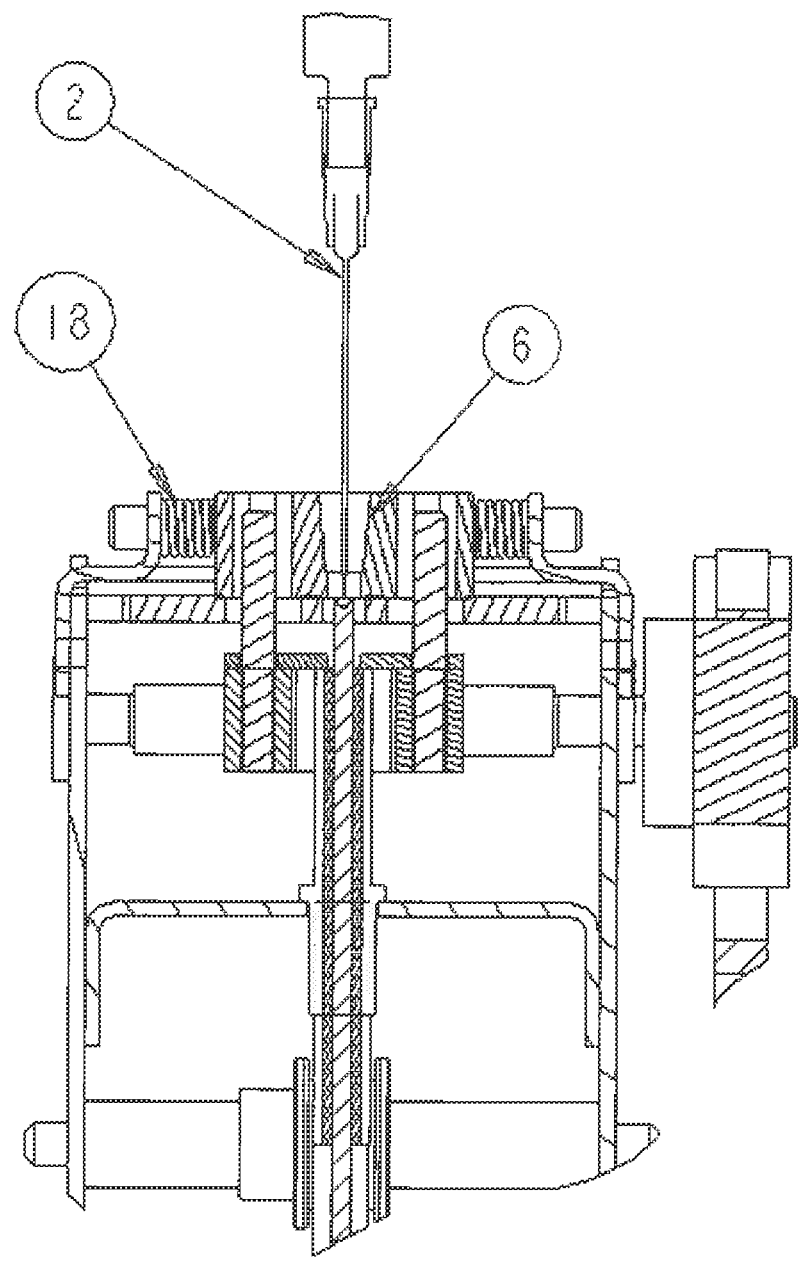
Figure 12:
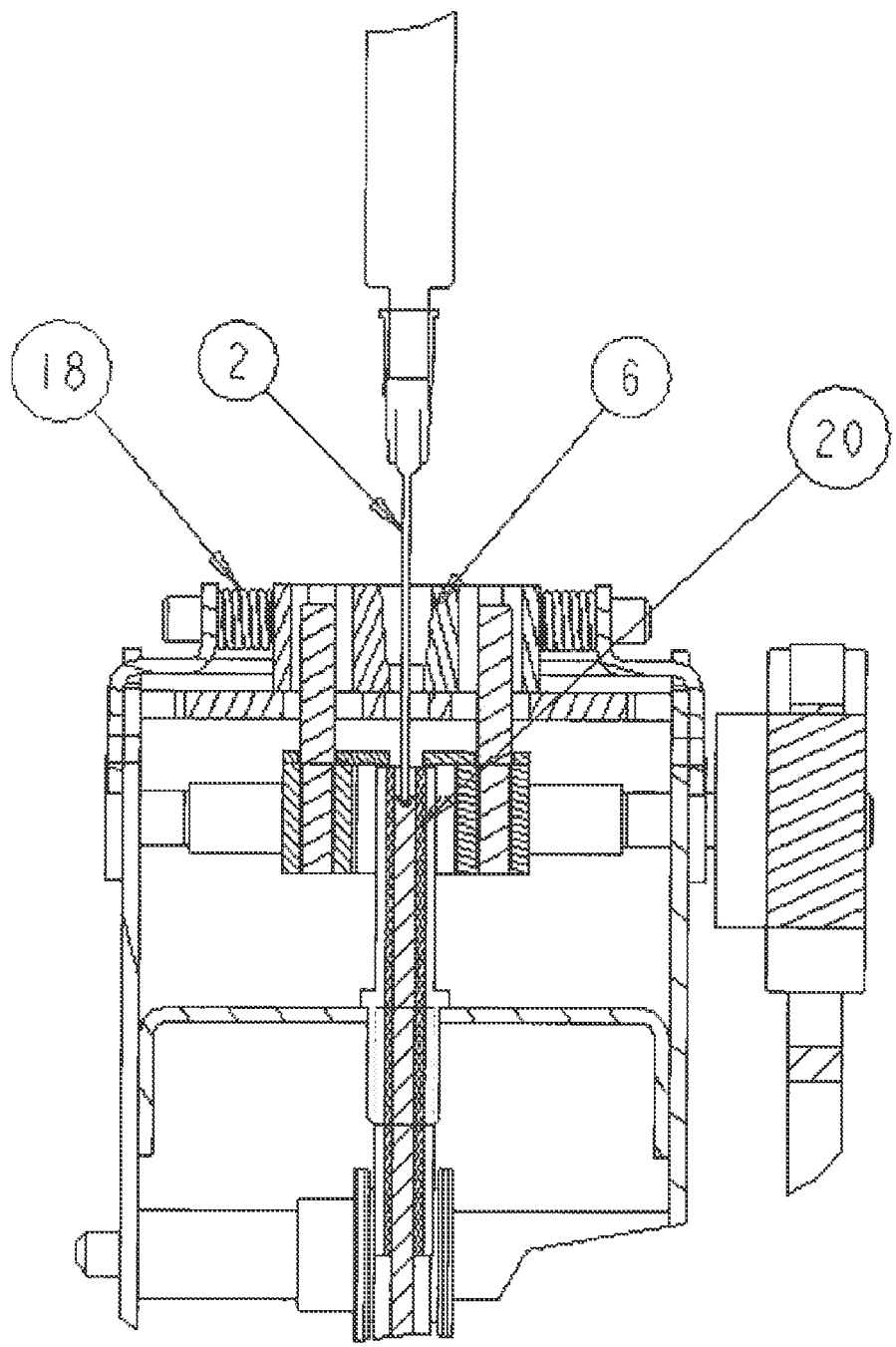
Figure 13:
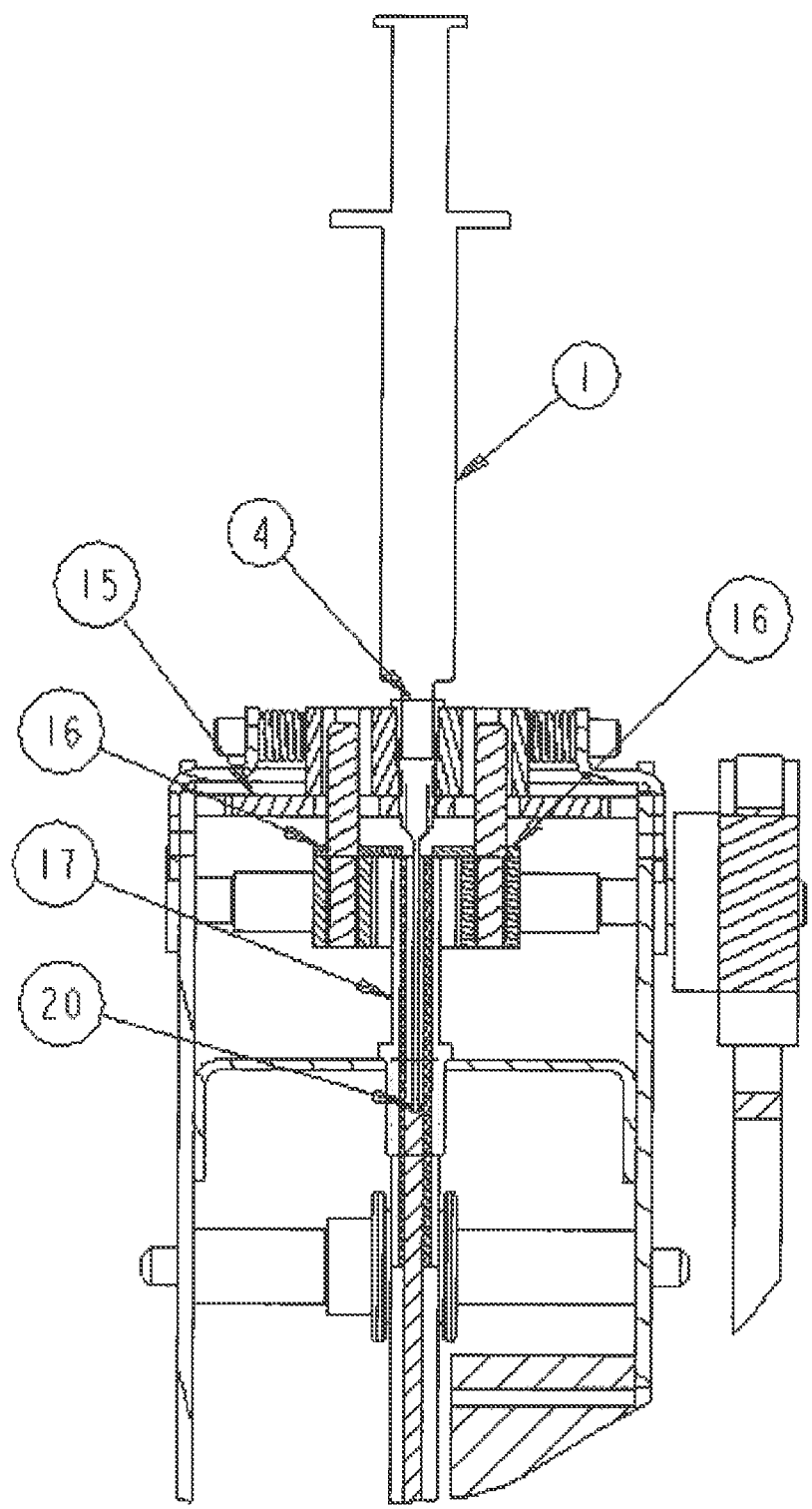
Figure 14:
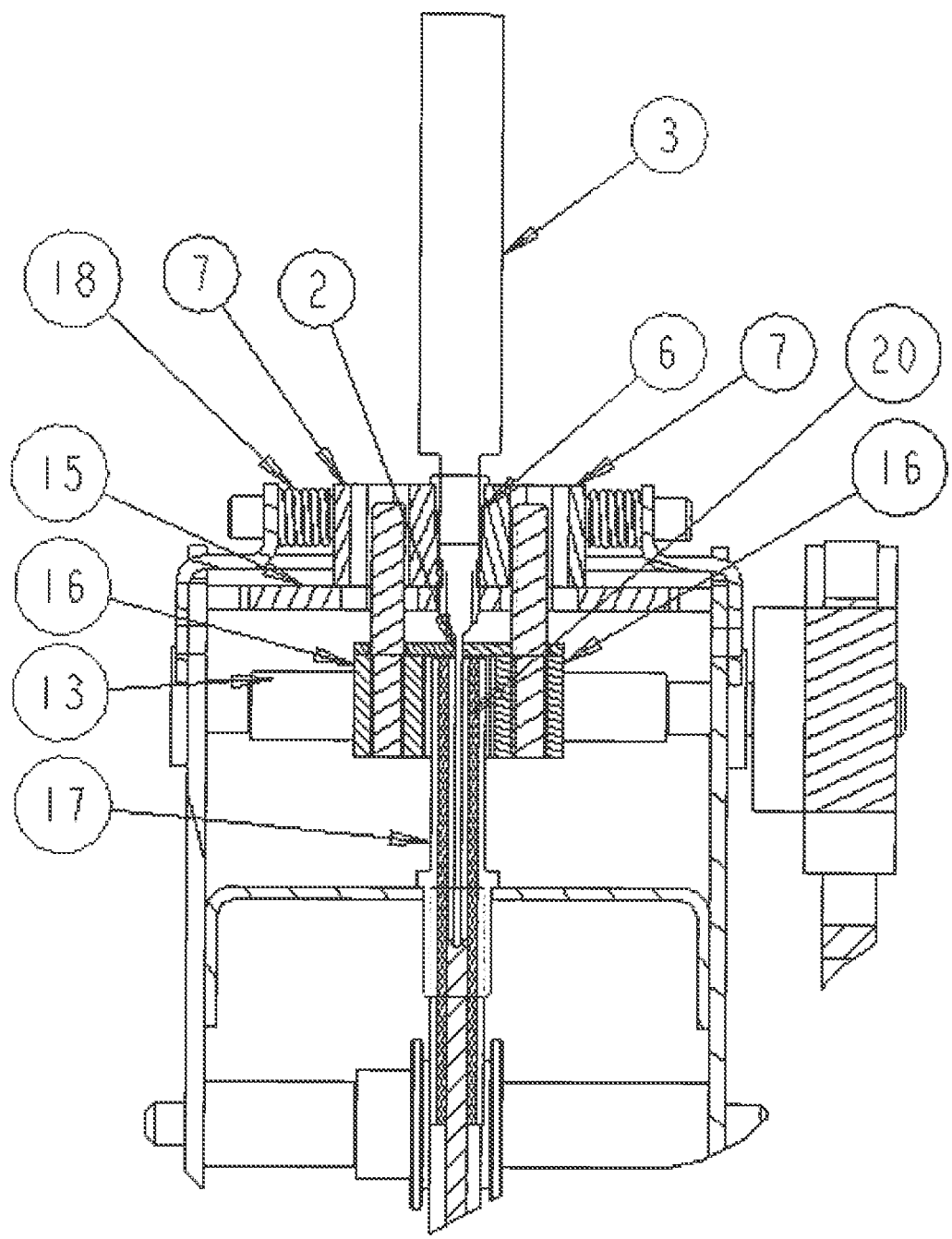
Figure 15:
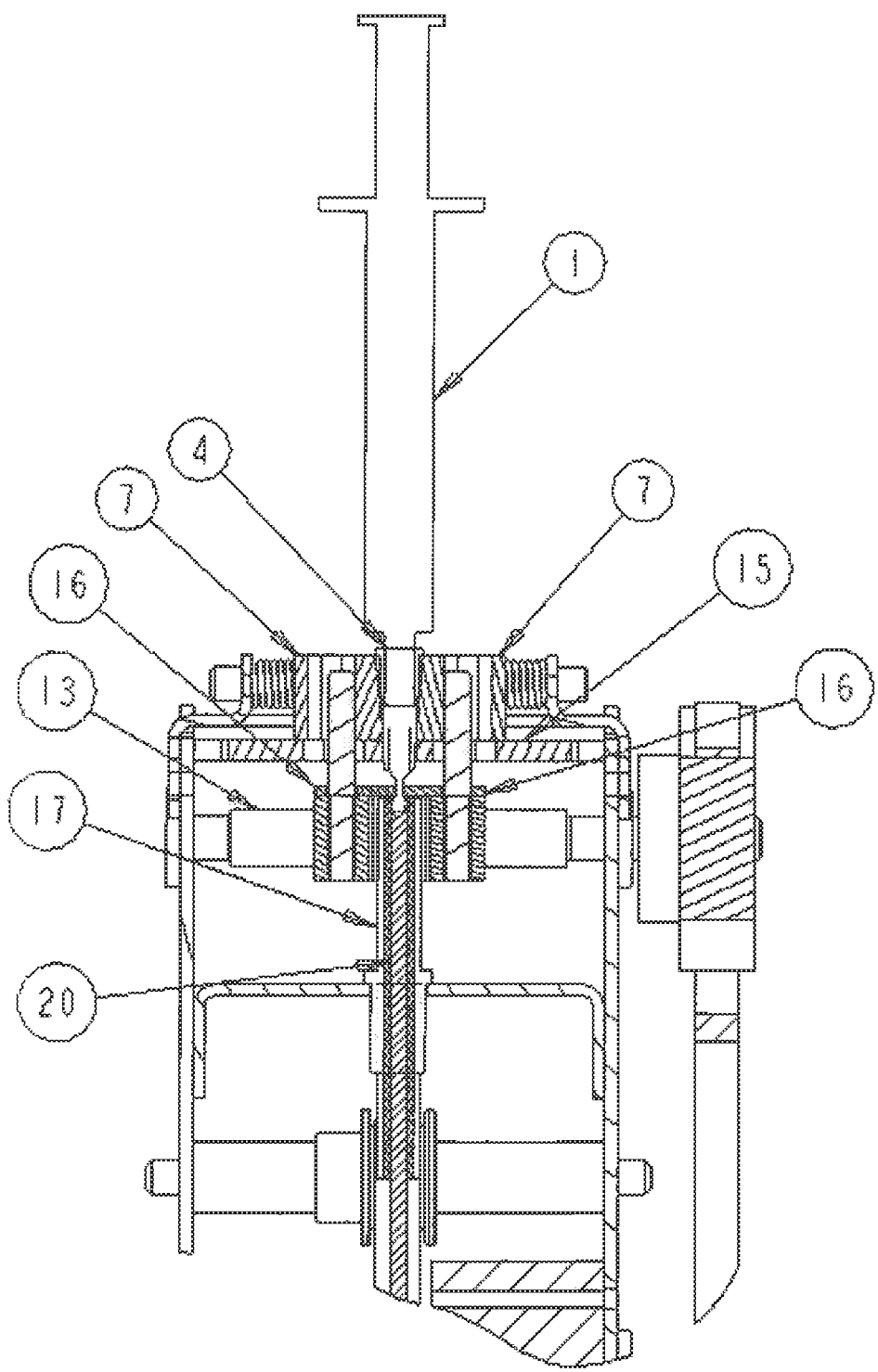
Figure 16:
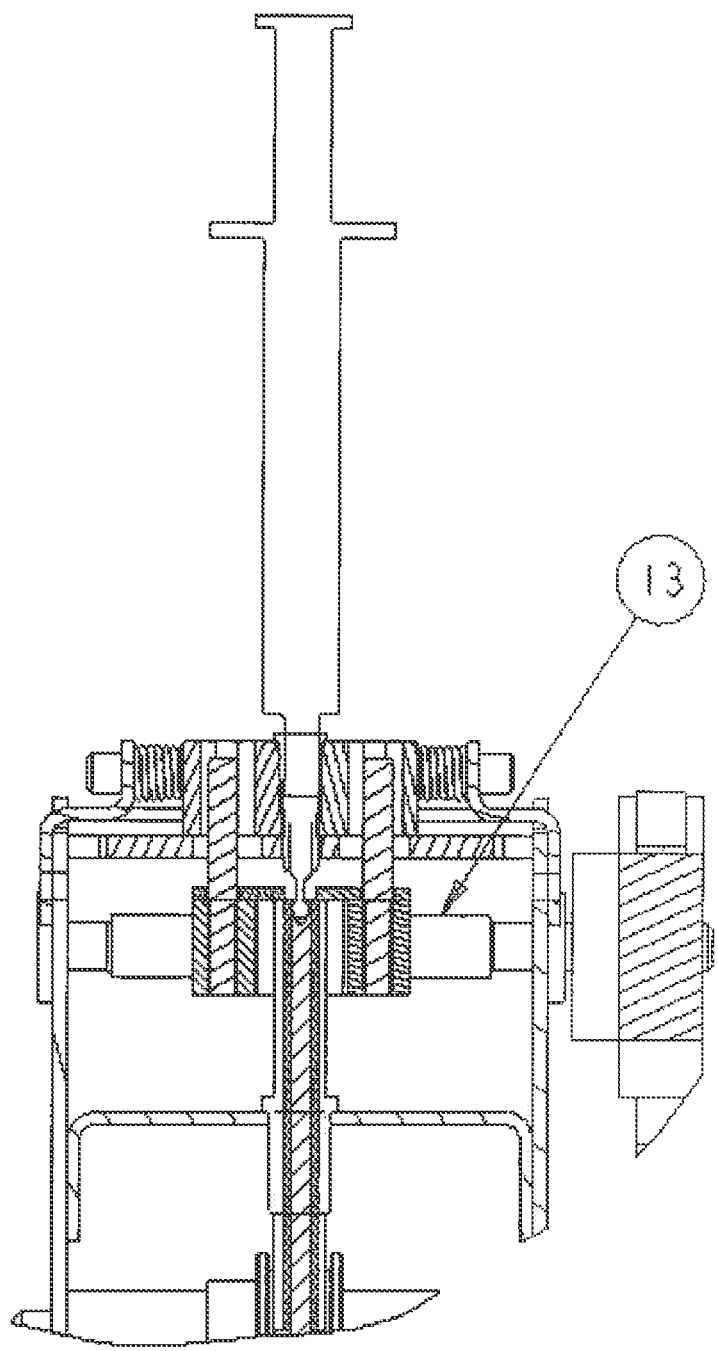
Figure 17:
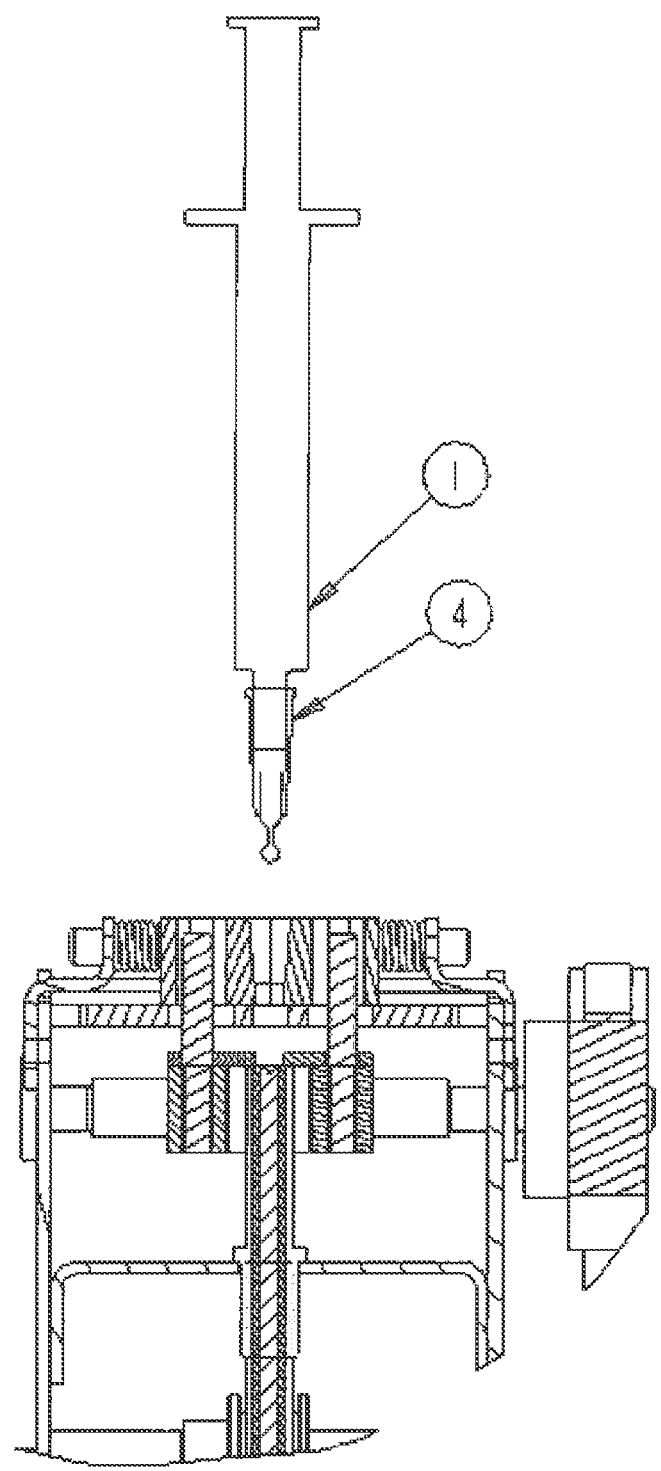
Figure 18:
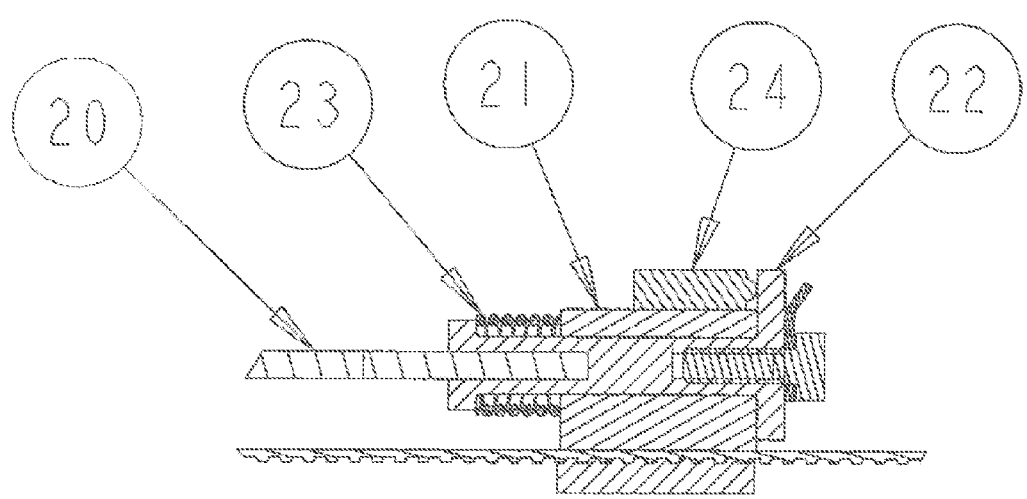
Figure 19A:
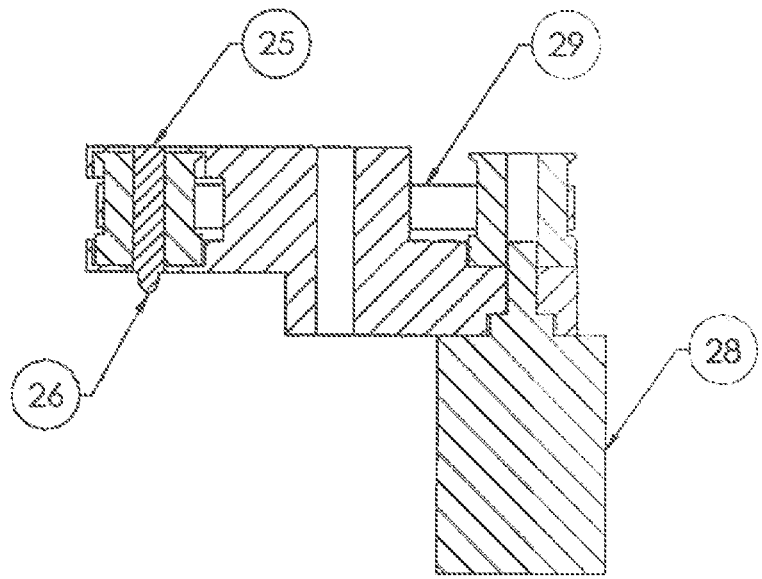
Figure 19B:
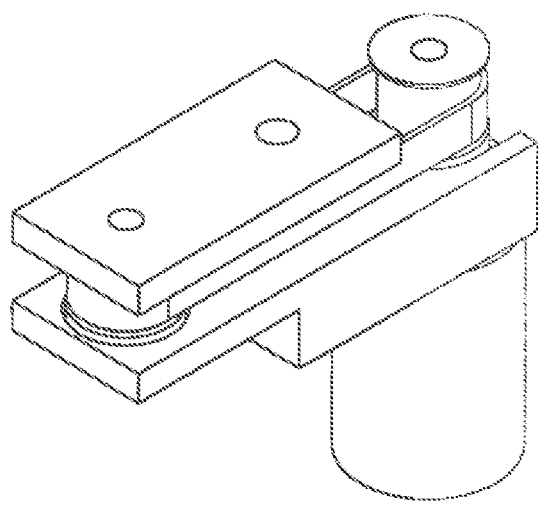

FIGS. 3a-e show further details of a principle of operation of a first embodiment of the invention;

FIG. 4 shows a perspective view of a second embodiment of the present invention;

FIG. 5 shows a detailed cross-section of a second embodiment of the present invention; and FIG. 6 shows a perspective view of an apparatus according to a second embodiment of the invention;

FIG. 7 shows a syringe assembly following processing by an apparatus according to an embodiment of the present invention;

FIG. 8 shows a partially exploded view of a third embodiment of the present invention;

FIG. 9 shows a cross-sectional view of a fourth embodiment of the present invention before destruction of the needle;

FIG. 10 discloses a cross-sectional view of a fourth embodiment of the present invention once destruction of the needle is complete;

FIG. 11 shows a cross-sectional view of a third embodiment of the present invention with the needle in position to be inserted into the device;

FIG. 12 shows a cross-sectional view of a third embodiment of the present invention with the needle partially inserted into the device;

FIG. 13 shows a cross-sectional view of a third embodiment of the present invention with the needle fully inserted into the device and the clamping electrodes about to close;

FIG. 14 shows a cross-sectional view of a third embodiment of the present invention with the needle fully inserted into the device and the destruction process about to commence;

FIG. 15 shows a cross-sectional view of a third embodiment of the present invention with the destruction process substantially completed with the coalesced needle cooling;

FIG. 16 shows a cross-sectional view of a third embodiment of the present invention with the cooled coalesced needle about to be withdrawn;

FIG. 17 shows a cross-sectional view of a third embodiment of the present invention with the coalesced needle having just been withdrawn;

FIG. 18 shows a cross-sectional view of a portion of a third embodiment of the present invention showing a detailed view of the sliding electrode mechanism; and FIGS. 19a and 19b show perspective views of an electrode cleaning mechanism forming part of a third embodiment of the present invention.

Figure 1:
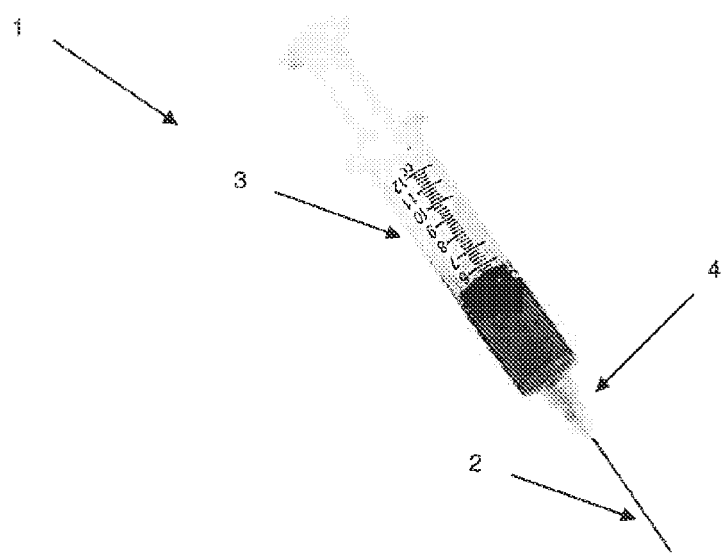
FIG. 1 shows a prior art syringe assembly.

FIG. 1 shows a standard disposable syringe 3, fitted with a hypodermic needle 2 to form a syringe assembly 1. Such an assembly 1 is used in a variety of medical situations. Typical uses include the administration of a medicine to a patient whereby the medicine in question is drawn up into the body of the syringe 3 via an insertion of the needle 2 into a vial or similar container of medicine. In some situations, the syringe assembly 1 is supplied pre-filled with a medicine and all that is required is for the practitioner to remove a sheath (not shown) from a needle 2 before the hypodermic needle 2 is used to administer the medicine. Another use of a syringe assembly 1 is to withdraw a sample (e.g. blood) from a patient. In this case, the syringe 3 is empty to begin with and is filled with blood by withdrawal of the plunger.

However the syringe assembly 1 is used in practice, there is always a problem of how to dispose of it safely after use.

Embodiments of the present invention provide apparatus to safely process the hypodermic needle 2 of a syringe assembly 1 after use.

Figures 2A, 2B:
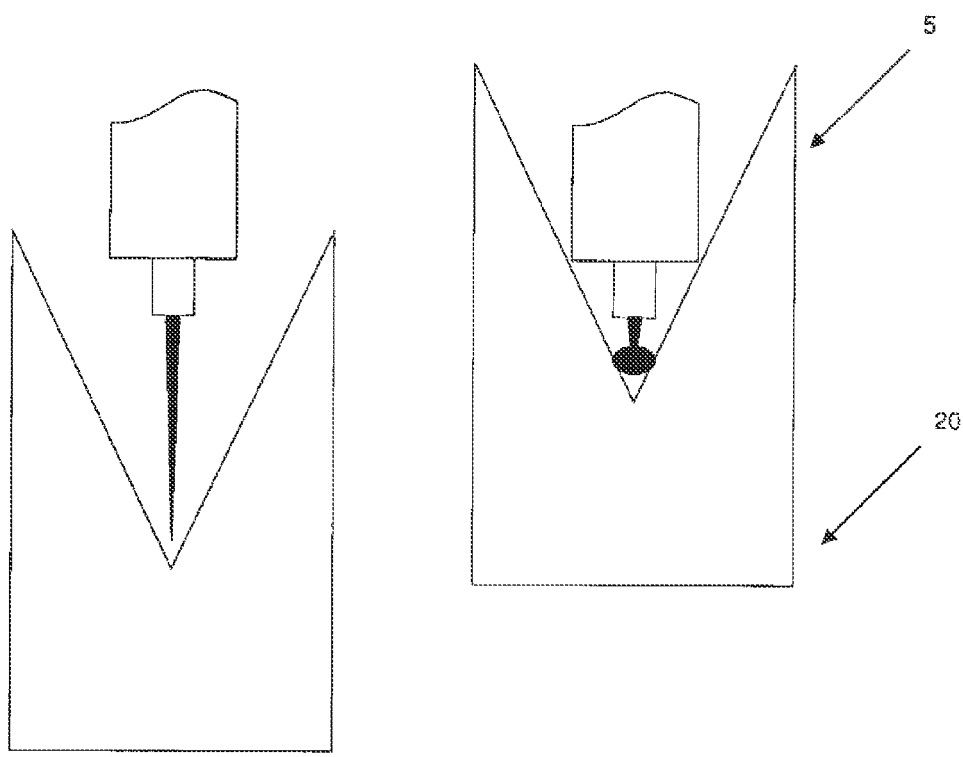
FIGS. 2a and 2b show a principle of operation of a first embodiment of the invention.

FIGS. 2a and 2b shows a principle of operation of a first embodiment of the invention. In use, a syringe assembly, 1 is introduced in a downwards direction into an apparatus for safely destroying the needle 2. The syringe assembly is clamped in position (not shown here, but described later). A voltage is applied across the length of the needle, from the clamp to the sharp end. The sharp end of the needle is contacted by a substantially concave or conical end 5 of electrode 20, and the applied voltage causes a current to flow through the needle, heating and thus, softening it.

Once the needle has softened to a sufficient degree, the electrode 20 advances upwards towards the hub 4. The concave end 5 of the electrode 20 tends to ensure that if the needle bends as it's being compressed, it will remain within the confines of the cone and be compressed into a compact mass as shown in FIG. 2b.

FIGS. 3a-3e show the stages involved in processing a needle in more detail. They show the needle and syringe being orientated vertically but, as will be described later, the orientation may be otherwise, particularly, horizontal.

Figures 3A, 3B, 3C, 3D, 3E:
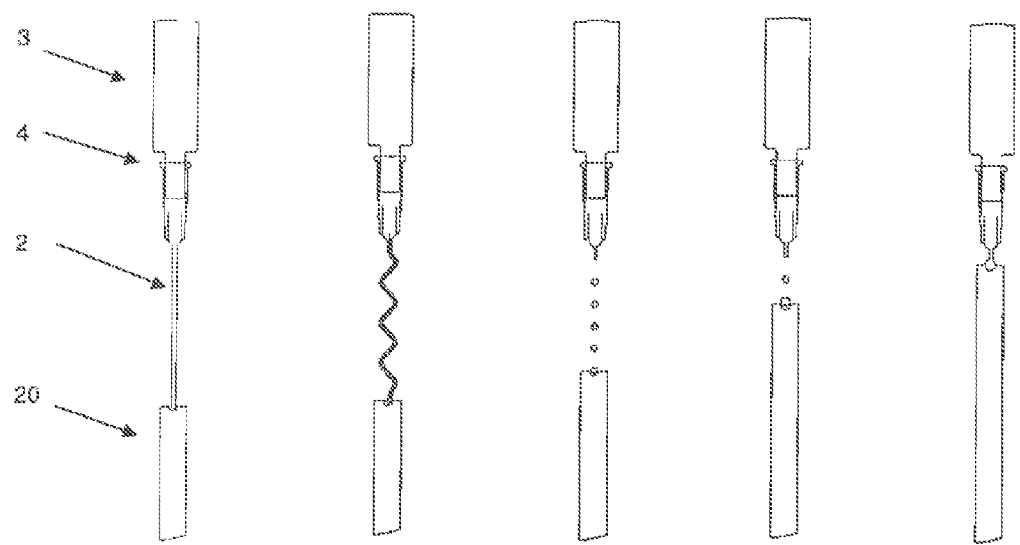

In FIG. 3a, the needle first contacts the concave end 5 of electrode 20. Once contact is made between the electrode 20 and the clamping electrode (not shown, but located adjacent the hub 4), a voltage is applied, causing a current to flow in the needle 2. At the same time, or slightly later, the electrode 20 is advanced towards the hub 4, so that the needle begins to compress. This is shown in FIG. 3b.

Depending on a number of factors, including the precise voltage applied and the physical characteristics of the needle, the voltage applied may cause the needle to heat so much that it melts. This scenario is shown in FIG. 3c where the needle is transformed into a series of molten metallic droplets.

The continued advance (see FIG. 3d) of the electrode 20 gathers these molten portions of the needle together until they coalesce in a single mass as shown in FIG. 3e.

The scenario shown in FIGS. 3a-e depicts the needle melting under the application of a voltage, but it will be appreciated that it is not necessary for the needle to melt, in order for the softened needle to be compressed by the electrode to yield a single mass of material.

It will be appreciated that the simplified series of events shown in FIGS. 3a-e could not be readily achieved in practice, particularly if the needle is positioned at any angle other than substantially vertical. In practice, the needle would not generally compress in on itself as shown in FIG. 3b, and the result would, accordingly, not be the compact single mass desired.

In practice, it is found that if the needle can be constrained during the compression operation, the repeatability and reliability of the process is much improved. Consequently, a second embodiment of the invention is shown in FIGS. 4-6.

FIG. 4 shows a perspective view of the apparatus 110, and further detail is shown in the sectional view of FIG. 5 and the isometric view of FIG. 6. The apparatus 110 comprises a housing 112 having an aperture 114 on one side thereof. The aperture 114 is arranged to receive the hypodermic needle 2 of the syringe assembly 1. The hypodermic needle 2 has a sharp point at one end and a hub 4 at the other, which is connected to the syringe 3. In use, the syringe assembly 1 is inserted into the aperture 114 until the hub 4 comes to rest against a stop plate 116 positioned beside the housing. Once the needle 2 has been fully inserted into the apparatus 110, the destruction process can begin. Full insertion of the needle is sensed by the actuation of a micro-switch (not shown) or similar device within the housing.

Upon sensing full insertion, the hub 4 is locked in position by means of an electrically operable clamping mechanism, which firmly grips the syringe assembly and holds the needle centrally within the aperture 114. The clamping mechanism comprises a pair of electrodes, which are operable by a pair of oppositely handed screw threads, mounted on a single shaft on which they are able to slide. In this way, rotation of the shaft causes both electrodes to move in unison towards either the open or the closed position. Importantly, due to the direct mechanical linkage of the pair of clamping electrodes, they will always close at exactly the same position, which allows the position of the needle in the aperture to be predicted reliably and consistently.

In the aperture 114, there is located a containment cylinder 118, which is arranged to receive the needle 2. The containment cylinder is preferably manufactured from a heat-resistant, durable material, such as glass, ceramic or coated steel.

Once inserted, the needle 2 resides substantially fully within a containment cylinder 118. Also positioned within the containment cylinder is piston 120. When the needle 4 is first inserted, piston 120 is located adjacent the end of the cylinder 118 nearest the aperture 114. The pressure of the user inserting the needle 4 causes the piston to be pushed back into the cylinder to accommodate the needle.

The piston 120 is arranged to provide a compressive force to the needle 2 within the cylinder 118. In a preferred embodiment of the invention, the compressive force is provided by a solenoid operable under user or automatic control. In other embodiments of the invention, the compressive force may be provided by a spring or other suitable means. The destruction process may be continuous or may comprise a number of separate stages.

In a first embodiment, once the needle is fully inserted and the lock 116 has firmly clamped it in place, a current is passed through the needle. The voltage is applied by the lock mechanism 116 and the piston 120 which acts as an electrode, thereby causing a current to flow in the needle. In this embodiment, a relatively small current is first applied which fuses the sharp tip of the needle to create a more substantial mass. Then, a larger current is applied which softens the needle sufficiently to allow it to be compressed.

The next stage involves the movement of the piston 120 to apply a compressive force to the softened needle, compressing the needle material into a compact mass, still attached to the hub 4.

The compressive force may be applied by a stepper motor, a solenoid, spring pressure, pneumatic force or can even be manually applied by the user.

Depending upon the exact composition and dimensions of the needle, it can sometimes be melted, rather than merely softened. In such an instance, the small beads of molten needle can be forced to coalesce or bond into a small mass in just the same way as has been described for the case where the needle is merely softened. The end result is much the same in either case—a compact mass with no sharp points, which can be disposed of without needing to be treated as a sharp.

The containment cylinder 118 tends to keep the needle 2 constrained within it. In its absence, the needle can tend to bend away from its axis and so the result of the compression may not always produce the desired effect. However, with the cylinder 118 in place, it forces the production of a small ball of material still attached to the hub 4.

Once the operation is complete, a period of time may be allowed to allow the compressed needle to cool down to a safe temperature. At the end of this period, the lock 116 is released, allowing the syringe assembly 1 to be removed. The hub 4 is now terminated in a small mass of compressed metal material with no sharp points, which may be removed manually and disposed of accordingly. The mass is substantially spherical, but other shapes having no sharp points or edges can be created, depending largely upon the profile of the piston 120.

FIG. 7 shows a perspective view of a syringe after processing, clearly showing the treated needle, in the form of an approximately spherical mass, attached to the hub 4.

Once the syringe assembly 1 is removed, the piston 120 may be moved so that it sits at the entrance of the cylinder 118, so that it's concave tip can receive another needle, or it may be moved back into the cylinder.

Embodiments of the invention are able to process many different gauges and/or composition of needle. In a preferred embodiment, various operational parameters may be altered by the user by means of one or more user-operable controls. For instance, a simple rotary switch can be provided, allowing the user to select one of a predefined number of programs, each corresponding to a particular type of needle. Alternatively, automatic sensing means can be provided, which are able to determine the length of the needle inserted, by reading the position of the piston 120 once the needle is fully inserted. The thickness of the needle can be determined by an optical sensor arranged to view the needle through the cylinder 118. Additionally, or alternatively, the resistance of the needle can be measured directly once it is fully inserted and this reading can be used to select a suitable operating profile.

An alternative embodiment of the present invention utilises an electrical induction process to soften the needle, rather than passing an electric current directly through the needle 2. In this embodiment, not shown, a coil for inducing a suitable current in the needle is arranged adjacent to, or surrounding, the containment cylinder 118. In all other material respects, the operation of this embodiment is the same as that already described.

A third embodiment of the invention is shown in FIGS. 8 and 11-17 and these represent an alternative but related means for safely disposing of hypodermic needles.

FIG. 8 shows a partially exploded perspective view of an apparatus forming a third embodiment of the present invention. It comprises a housing 12 which is approximately cylindrical in shape and comprises a handle for ease of transportation. Located within the housing is a mechanism for processing the hypodermic needle 2 of an inserted syringe assembly 1. The detailed operation of the mechanism will follow shortly. At one end of the housing 12 is provided an end plate which includes an aperture 14 through which is inserted the hypodermic needle 2 of the syringe assembly 1. The operation of the mechanism is essentially automatic following insertion of the needle.

FIGS. 9 and 10 show detailed views of a fourth embodiment of the present invention. This embodiment is broadly similar to the second embodiment, previously described in that the needle is not constrained during compression. The mechanism and operation of this fourth embodiment, apart from the lack of constraining means for the needle is identical with the third embodiment shown in general in FIG. 8 and in more detail in the description related to FIG. 11-17.

FIG. 9 shows a partial cross-sectional view of the needle destruction mechanism once a needle 2 has been introduced. For ease of illustration, parts of the apparatus which are not necessary for an understanding of the operation of embodiments of the invention have been removed from the following drawings. In a similar way to the previously described embodiments, upon insertion into the apparatus, the needle 2 at the tip of the syringe 1 contacts the concave end 5 of electrode 20, said electrode 20 being movable within the body of the apparatus. Upon being fully inserted into the apparatus, the mechanism is operable to firmly clamp the hub 4 of the syringe 1 in place and then to begin the needle destruction process.

FIG. 10 shows a partial cross-sectional view of the third embodiment of the invention once the needle destruction process has nearly completed. In this view, the electrode 20 has travelled from the position shown in FIG. 9 and has compressed the needle 2 so that it is no longer elongate and sharp but is rather an approximately spherical mass of metal located at the end of the hub 4.

FIGS. 11-17 show in detail various stages of the needle destruction process in a third embodiment of the present invention.

FIG. 11 shows a partial cross-sectional view through a third embodiment of the present invention at the point where a needle 2 is just about to be introduced to the apparatus. The needle 2 is passed through the aperture 14 on the end surface of the apparatus and, located within the aperture, is a pair of guide blocks 7 which are further provided with a central conical channel 6 which is operable to accept the needle and guide it accurately such that the tip of the needle aligns properly with the centre and end 5 of the sliding electrode 20. The guide blocks 7 are each provided with one half of the conical channel such that when the guide blocks 7 are mated together, the larger diameter formed at the exterior of the conical channel easily accepts the needle tip 2 and guides it to the smaller diameter of the conical channel which is situated adjacent the clamping electrodes 16. This ensures that the needle aligns as required with the tip of the sliding electrode 5. The guiding blocks 7 are mounted in the apparatus such that they can slide parallel to the access of the clamping electrode 16 which is situated below them as shown in the figures. The guide blocks 7 are provided with springs 18 that return them towards the mated position, i.e. the position in which they contact each other. A centrally located projection from the mounted frame or a similar feature ensures that when they are mated together, they are constrained in such a way that the smaller diameter of the conical guide channel 6 is directly aligned with the centre of the end of the sliding electrode 20.

Each of the clamp electrodes 16, located below the guide blocks 7, is provided with a drive pin that locates in a recess in the corresponding guide block 7 above it. The drive pins and their corresponding recesses in the guide blocks are designed with suitable clearances so that when the electrodes 16 move apart, initially the guide blocks 7 do not move and remain mated together under the spring force provided by springs 18. When the electrodes have moved apart sufficiently to allow the sliding electrode 20 to pass between them, the guide blocks will also start to separate. This feature enables two guide blocks 7 to be fully mated together but with the clamp electrodes 16 separated and the concave end 5 of the sliding electrode 20 positioned close to the lower surface of the guide blocks ready to accept a needle 2. This ensures that the needle 2 is always accurately guided into the centre of the concave end 5 of the sliding electrode 20.

FIG. 12 shows the situation in which the needle 2 is partially inserted into the apparatus. It can be seen that when a needle 2 is inserted through the conical guide channels 6 and makes contact with the sliding electrode 20, the sliding electrode will tend to start to retract under pressure provided by the user. The electronic control system is operable to detect this action and then to activate a drive device to separate the two clamp electrodes 16 and hence the guide blocks 7. The control system is operable to detect this action by use of a micro switch located between the sliding electrode 5 and its driving mechanism.

The separation of the guide blocks 7 in this way allows the hub 4 of the needle 2 to make contact with a switch plate 15 which is operable to provide a further signal indicative of the fact that the needle is fully inserted.

Once the needle has been detected as having been fully inserted, the control system is then operable to initiate the destruction process.

FIG. 18 shows a close up detailed view of the means by which the electrode 20 is moved towards the needle 2. The electrode 20 must be moved in order to ensure that there is continuous or nearly continuous contact between the electrode and the needle after the destruction process proceeds. FIG. 18 shows how the electrode 20 is moved by a toothed belt which in turn is driven by a stepper motor (not shown). Attached to the toothed belt is a movable block 21 through which a metal sleeve 22 freely passes. At the ends of the sleeve 22, fixed collars are provided to restrict its movement and to contain the pre-compressed delivery spring 23. A threaded hole is provided in the sleeve 22 into which is screwed the threaded end of the sliding electrode 20. At the opposite end of the sleeve 22 there is provided an attachment point for the connection of the power supply to the sliding electrode 20 and an extension portion that operates a micro switch 24 that is affixed to the moving block 21.

When the apparatus is ready to accept the needle 2 for destruction, the electronic control system is operable to position the tip 5 of the sliding electrode 20 adjacent to the underside of the guide blocks 7 with the associated stepper motor held in a stationary position, resisting rotation and thus movement of the toothed belt. Upon insertion of the needle 2 through the central conical channel 6 in the guide blocks 7, the tip of the needle will contact the concave end 5 of the sliding electrode 20. Further pressure to insert the needle 2 into the device will result in the delivery spring 23 being compressed and a circuit being completed by activation of the micro switch 24. The completion of this circuit energizes the stepper motor, allowing it to turn smoothly and consequentially to allow the needle to enter the device more fully. If pressure on the needle is relaxed, the motor will stop until said pressure is reapplied and this circuit completed once more. The operation of this feature of the device ensures that entry of the needle 2 into the device feels smooth and controlled, which would not be the case if the needle 2 simply pushed the belt along and rotated the stepper motor itself. In such a case, the movement would be jerky as the motor tends to resist the movement with its intrinsically uneven characteristics. Such a characteristic would be undesirable to the user, and the active operation of the stepper motor in this way results in a more controlled feel to the user.

Turning now to FIG. 13, which shows the situation where the needle has been fully inserted and the electronic control system has sensed full insertion by the action of the hub 4 contacting the switch plate 15. The root of the needle 2 is then gripped firmly in position by means of an electrically operable clamp mechanism comprising a pair of clamp electrodes 16 which are operable to firmly grip the needle and hold it centrally relative to the sliding electrode 20. The clamp mechanism further comprises a shaft or shafts on which the clamp electrodes 16 run. The clamp electrodes 16 are operable by a pair of screw threads of opposite handing, on the shaft 13. In this way, rotation of the shaft causes both clamp electrodes 16 to move in unison towards either the open or the closed position. Since they are in direct mechanical communication, they will always close towards the same position which enables the position of the needle in the aperture to be predicted reliably, consistently and accurately. The threaded shaft or shafts are driven by a toothed belt, in turn driven by a stepper motor (not shown).

Situated within the apparatus and adjacent to the clamp electrodes 16, there is a containment cylinder 17 which is arranged to receive the needle. The containment cylinder 17 is formed from a heat resistant and durable material such as glass, ceramic or metal. It may optionally be sheathed in a further cylinder which is mounted into the framework of the apparatus in such a way that it may be easily removed and replaced for routine service.

Once inserted into the apparatus, the needle 2 resides substantially within the containment cylinder 17. Also positioned within the containment cylinder 17 is a sliding electrode 20 which is dimensioned to provide a close fit within the cylinder 17. When the needle 2 is first inserted, the sliding electrode 20 is located adjacent to the end of the containment cylinder 17 and nearest the clamp electrodes 16. The force applied by the user inserting the needle 2 causes the sliding electrode 20 to be pushed back within the containment cylinder in order to accommodate the needle. This motion, under control of the stepper motor, has been described previously.

The sliding electrode 20 is arranged to provide a compressive force to the needle 2 within the containment cylinder 17. In a preferred embodiment of the invention the compressive force is provided by a stepper meter operable under automatic electronic control. It is possible, in other embodiments of the invention, that the compressive force may be provided by gravity, a spring, a motor, a solenoid or by pneumatic means. The destruction process may occur in a continuous manner or it may comprise a number of separate discreet stages.

FIG. 14 shows the situation once the needle 2 is fully inserted and has been firmly gripped between the clamp electrodes 16. A current is then passed through the needle from the sliding electrode to the clamp electrodes, passing through the needle 2. In the embodiment shown, a relatively small current may be first applied to the needle together with a force to the needle tip via the sliding electrode 20 which is either steady or intermittent via a series of small impacts. The purpose of this is to soften and deform the sharp tip of the needle to create a more substantial contact area. A larger contact area enables larger currents to be subsequently applied to the needle 2 resulting in reduced sparking at the sliding electrode 20 and hence a lower degree of contamination in the containment cylinder 17.

FIG. 15 shows the situation after a larger current has been applied, which softens the needle 2 further, and is sufficient to allow it to be deformed and compressed by the motion of the sliding electrode 20 which travels towards the hub of the needle and applies a compressive force to the softened needle. This compresses the needle material into a compact, coalesced mass which remains attached to the hub of the syringe 4.

Depending upon the exact composition and dimensions of the needle, the needle may be melted, rather than being merely softened. In such case, small beads of molten needle material can be produced and these can be forced to coalesce or bond into a small mass in the same way as has been described for the case where the needle is merely softened. The end result is similar in either case and is a coalesced needle, i.e. a mass attached to the hub without a sharp point.

The containment cylinder 17 acts in the same way as has been described in relation to the second embodiment in that it tends to keep the needle constrained within it. In its absence, the needle would tend to bend away from its axis and so the result of the compression may not always produce the desired effect and can result in merely a bent and still sharp needle. With the containment cylinder in place, a compact ball of material still attached to the hub tends to be reliably produced.

Once the needle has been compressed and the mass of metal has coalesced, a period of time is allowed in order that the coalesced needle can cool down to a safe handling temperature. During this cooling down time, the clamp electrodes 16 are used to maintain the needle in its position within the apparatus. This prevents the user withdrawing the coalesced needle prematurely. This scenario is shown in FIG. 16.

Once the cooling period has expired, the clamp electrodes 16 are released and the syringe assembly 1 and coalesced needle can be removed safely as shown in FIG. 17.

Once the syringe assembly 1 is removed from the apparatus, the sliding electrode 20 is positioned so that it sits at the entrance of the containment cylinder 17 such that its concave tip 5 can receive another needle. Alternatively, once the clamp electrodes 16 are released, the sliding electrode 20 may be moved further down the cylinder instead.

The syringe assembly 1 now comprises a hub 4 terminated in the coalesced mass of the needle material. The mass is arranged to be substantially spherical, although the exact shape is largely dependent upon the concave profile of the tip 5 of the sliding electrode 20. Any suitable shape may be used provided that the end result is essentially smooth and has no protruding sharp points. Further, the coalesced needle material has the effect of sealing the internal bore of the needle thereby inhibiting fluid leak from the syringe. It is, of course, possible that a used syringe may contain one or more dangerous materials and the destruction process described herein is intended to prevent any such materials harming a user of the used syringe. Since the coalesced needle material has no sharp points, it may be disposed of via normal clinical waste rather than being treated as a sharp and having to be disposed of via the more expensive sharps bin procedure.

The apparatus further comprises an electronic control system which is operable to control the operation of all features of the device including the clamp electrodes, the stepper motor for locating the sliding electrode and the current supply which is applied to the needle to destroy it. The electronic control system comprises a suitably programmed microcontroller or microprocessor. Alternatively, it may comprise a custom integrated circuit.

It is found that larger needles (i.e. those of greater length or greater diameter) require greater heat energy to process than smaller ones and, also, the sliding electrode 20 must travel further to adequately compress the needle. It is therefore apparent that different needle types and sizes require different current and motion of the sliding electrode 20 if they are to be successfully processed and made safe. The electronic control system therefore comprises a range of different operating profiles which may be either pre-stored or calculated on the basis of a particular needle and these operating profiles are optimised for each different needle type and size.

A particular operating profile for a given needle type and size can include instantaneous set values for needle current versus time such that an appropriate current can be applied at exact time points during the needle processing. In this way, the previously mentioned technique of softening just the tip of the needle by use of a lower current at the initiation of the process can be managed in a straightforward fashion.

A particular operating profile also includes instantaneous values for the position of the sliding electrode 20. Such values can also determine the velocity of the sliding electrode as each position is related to time. Typically, during processing of a needle, the total time that current may be applied to the needle is between 0.2 and 2 seconds. The sliding electrode 20 may be in motion for a similar but not necessarily coincident period. The current applied to the needle is modulated to predetermined or instantaneously calculated values many times per second. Typically, a profile may determine values for current every 5 to 50 ms. Likewise, the set position of the sliding electrode 20 may be updated every 5 to 50 ms.

In a preferred embodiment the means to determine the current in such periods is by switching the current fully on or off to produce an average current equal to that desired, according to the on/off ratio of the switched current. This technique is commonly known as pulse width modulation (PWM). The switching period may be fixed or variable but must be less than that for the determined current period. It is also preferred that the switch period be less than ten times the thermal time constant of needle heating such that the needle may not be melted by a single or small number of on pulses. Typically the on/off switch period is in the range 0.2 to 20 mS.

The control system may be arranged to determine the current more accurately if a measure of the actual instantaneous current is provided by, for instance, a feedback current measurement. One way of achieving this is by configuring the control system to determine the instantaneous current in the needle by calculation after measuring the voltage this current develops across a suitable sense resistor connected in series. This method is simple but requires a suitable power resistor and some energy is wasted as heat in that resistor.

Alternatively, the current can be determined using a suitable Hall-effect current sensor, also connected in series. This method avoids significant energy losses but adds cost for a suitable Hall-effect sensor. A preferred technique for needle current measurement uses a much smaller, scaled current in parallel to the needle current. This scaled current is proportional to the main needle current by a known ratio. The main current may therefore be determined by calculation after measuring the scaled current. This is achieved by measuring the voltage the scaled current develops across a suitable resistor. In this case the measurement is simple and possible without significant heat loss because the scaled current is very much smaller than the main needle current. The scaled current may conveniently be achieved using a semiconductor switch for the main needle current that features a parallel current path scaled to that of the main current. An example of a suitable semiconductor for the switch is a high current MOSFET with two parallel, but scaled sources. Typical parts currently available in the market use scale ratios in the range 1000:1 to 50000:1

In a preferred embodiment of the apparatus, a visual display driven by the electronic control system will indicate one or more operating parameters including the readiness of the apparatus to accept a needle for destruction, the stage of the destruction process and the status of many of the operating parameters, e.g. the number of needles processed since the last battery recharge, and charge remaining in the battery.

Over time, metallic and/or other debris may build up in the concave recess 5 in the end of the sliding electrode 20. This debris may inhibit the conduction of the electric current through the needle 2 or otherwise hamper the destruction process. When such debris is either visible to the user or is evident through one or more failed needle destruction attempts, a semi or fully automatic process to clean the recess can be initiated.

FIGS. 19a and 19b show schematic and perspective views respectively of the self cleaning device which forms part of the apparatus. The position of these devices can be seen clearly in FIG. 8. FIG. 19a shows a schematic cross sectional view of the self cleaning apparatus and it comprises a small, spherical or similarly shaped rotary cutter, grinder or brush 25 whose end point 26 protrudes from the apparatus and is slightly smaller than the end concave surface 5 of the sliding electrode 20. This cutter 25 is positioned in suitable plain or ball bearings so that it is free to rotate and may be driven by an electric motor 28 by a toothed or plain belt 29.

The cutter axis is set parallel to that of the sliding electrode 20 and the cutter may be moved either manually or automatically to align it to be coaxial with the sliding electrode 20. The cleaning device is moved manually into position by a lever or similar projection accessible from the outside of the apparatus. When the cutter is correctly located coaxially with the sliding electrode 20 a micro switch (not shown) will be actuated and the cleaning sequence will be initiated automatically by the electronic control system. In the cleaning sequence, power will be supplied to the electric motor 28 and the cutter 25 will rotate. At the same time, the sliding electrode 20 is advanced towards the rotating cutter 25, thereby causing the concave end 5 of the sliding electrode 20 to contact the cutter point 26. A fan is provided which is also driven by the electric motor 28 to generate a focussed jet of air to remove any debris loosened by the cutter 25. A suitable collection device or container which is removable from the apparatus is provided to accept and collect the debris.

From use, further debris may build up over time on the internal wall of the cylinder 17. This may cause friction between the internal surface and the sliding electrode 20. This may inhibit free movement of the electrode and hence impair the destruction process. In order to address this potential problem, a process may be used to clean the internal surface of the cylinder whereby the sliding electrode 20 travels within the cylinder 17 over an extended distance for a predefined number of cycles. This effectively displaces the debris to the outside of the cylinder 17 where it may be collected for later disposal. To assist this process, the outer surface of the sliding electrode 20 may be provided with a number of shallow annular grooves to assist the debris displacement process. Such a cleaning process may be run periodically or even after every needle destruction, as needed. Alternatively, it may only be initiated after one or a certain number of aborted needle destructions has been encountered.

Embodiments of the invention comprise safety features which prevent objects not closely resembling hypodermic needles being inserted into the apparatus. Such safety features can comprise physical restrictions which prevent objects other than syringes being inserted into the device, or more sophisticated devices which are able to measure the resistance of an inserted object to ascertain whether it is, or is likely to be, a hypodermic needle.

The power to operate the apparatus can be provided from one or more battery cells, preferably rechargeable cells, which allow the apparatus to be used away from a power source. Alternatively, or additionally, the power can be provide from a main voltage supply.

Throughout this specification, the term hypodermic needle has been used. The skilled person will readily recognise that this term can include needles fitted to syringes, as has been described in detail, but the term hypodermic needle is also intended to include other needles used to introduce/remove fluids to/from the human or animal body. Other such needles are characterised by being of a generally tubular metallic composition having at least one sharpened end. A specific type of needle explicitly included in the definition is the needle used with a cannula.

Different embodiments of the present invention may include one or more features from any of the described embodiments, where any such features are not mutually contradictory. For brevity of description, certain features have been described in relation to one particular embodiment, but any feature may be incorporated into any of the embodiments described herein.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. An apparatus for processing a hypodermic needle, comprising:
    a containment cylinder for receiving the needle;
    a first electrode for contacting the needle near a first end;
    a second electrode, arranged as a piston, movable within the containment cylinder, for contacting the needle at its sharp end; and
    a control system, operable to cause a current to flow in the needle between said first and second electrodes, whereby said current causes the needle to soften and wherein the second electrode is arranged to move within the containment cylinder and to provide a compressive force to the needle.

2. The apparatus of claim 1 wherein the containment cylinder is arranged such that as the second electrode provides the compressive force, the mass of the needle is contained within the cylinder.

3. The apparatus of claim 1 wherein the control system causes a current to flow in the needle by applying a voltage directly to the needle or by inducing a current in the needle.

4. The apparatus of claim 1 wherein the second electrode comprises a piston.

5. The apparatus of claim 4 wherein the piston comprises an indentation in which, in use, rests the sharp tip of the needle.

6. The apparatus of claim 1 further comprising locking means to grip the needle at a hub and secure it in place for subsequent processing.

7. The apparatus of claim 6 wherein the locking means comprises a pair of slidable clamps mounted on a common shaft, each clamp being driven by a relatively opposite-threaded screw thread.

8. The apparatus of claim 7 further comprising a pair of guide blocks, each forming one half of a conical channel such that when the guide blocks are mated together, the conical channel is operable to guide the needle.

9. The apparatus of claim 4 wherein the compressive force is provided by one of a stepper motor, a solenoid, a spring, or manual force.

10. The apparatus of claim 1 wherein means are provided to select one of a plurality of operational programs.

11. The apparatus of claim 10 wherein the means for selecting one of a plurality of operational programs comprises means for determining at least one of a set of physical properties of possible needles.

12. The apparatus of claim 11 wherein the set of physical properties includes one or more of: length, thickness and electrical resistance.

13. The apparatus of claim 3 wherein the voltage is applied or the current is induced intermittently.

14. The apparatus of claim 13 wherein in the case where voltage is applied directly to the needle, a first relatively smaller current is applied in order to deform the tip of the needle to create a larger contact area.

15. The apparatus of claim 1 further comprising means for removing residue from the apparatus.

* * * * *